United States Patent [19]
Levon

[11] 3,962,274
[45] June 8, 1976

[54] 1-AZIDOALKYLIMIDAZOLES
[75] Inventor: Ernest F. Levon, Evanston, Ill.
[73] Assignee: G. D. Searle & Co., Chicago, Ill.
[22] Filed: Aug. 11, 1975
[21] Appl. No.: 603,336

[52] U.S. Cl................................ 260/309; 424/273
[51] Int. Cl.$^2$...................................... C07D 403/06
[58] Field of Search.................................... 260/309

[56] References Cited
FOREIGN PATENTS OR APPLICATIONS
2,211,454  10/1972  Germany............................ 260/309

OTHER PUBLICATIONS
Neugebauer et al., Chem. Abst., 1960, vol. 54, columns 13922–13924.
Lancini et al., Chem. Abst., 1966, vol. 65, col. 700.
Usher, Chem. Abst., 1968, vol. 69, No. 5557w.

*Primary Examiner*—Natalie Trousof
*Attorney, Agent, or Firm*—John M. Brown

[57]  ABSTRACT
Preparation and the antimicrobial and antihypertensive properties of 1-azidoalkylimidazoles and their salts are disclosed.

10 Claims, No Drawings

1-AZIDOALKYLIMIDAZOLES

This invention relates to 1-azidoalkylimidazoles and processes for the preparation thereof. More particularly, this invention provides new, useful, and unobvious chemical compounds of the formula

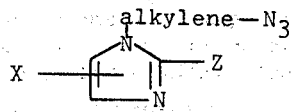

wherein X represents hydrogen or nitro and Z represents hydrogen, alkyl, or phenyl optionally substituted by halogen.

The alkylene denominated in the foregoing formula preferably contains more than 1 and fewer than 5 carbons, thus being typically 1,2-ethanediyl, 1-methyl-1,2-ethanediyl, 1,1-dimethyl-1,2-ethanediyl, 1,2-propanediyl, 2-methyl-1,3-propanediyl, 1,4-butanediyl, or like bivalent, saturated, acyclic, straight- or branched-chain, hydrocarbon grouping of the formula $$-C_xH_{2x}-$$

wherein $x$ represents a positive integer amounting to at least 2 but not more than 4.

Among the alkyls represented by Z in the introductory formula, lower alkyls are preferred, which is to say methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain, hydrocarbon groupings of the formula $$-C_yH_{2y+1}$$

wherein $y$ represents a positive integer less than 8. The halophenyls represented by Z are those in which preferably 1 but as many as 5 halogens, alike or different, are present. Positioning of these halogens (fluorine, chlorine, bromine, and/or iodine) relative to the point of attachment of the phenyl to the imidazolyl nucleus or, where more than 1 is present, to each other is not critical.

Equivalent to the foregoing basic amines for the purposes of this invention are the non-toxic acid addition salts thereof having the formula

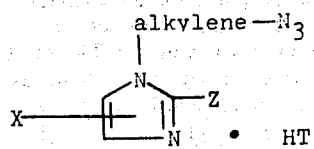

wherein the alkylene, X, and Z are as previously described and T represents 1 equivalent of an anion — for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like — which, in combination with the cationic portion of a salt aforesaid, is neither biologically nor otherwise unsuitable.

Preferred embodiments of this invention are the 2-alkyl-1-azidoalkyl-5-nitroimidazoles and their salts contemplated, albeit 2-desalkyl, 2-phenyl, 2-halophenyl, 4-nitro, and/or 5-desnitro analogs thereof are, as aforesaid, all within the purview of the instant disclosure.

The compounds to which this invention relates are useful by reason of their valuable biological properties. For example, they are antimicrobial agents adapted to inhibit or prevent the growth of bacteria such as *Bacillus subtilis*, *Salmonella paratyphi A*, *Staphylococcus epidermidis*, *Clostridium perfringens*, and *Desulfovibrio desulfuricans;* protozoa such as *Trichomonas vaginalis* and *Tritrichomonas foetus;* fungi such as *Trichophyton mentagrophytes;* and algae such as *Chlorella vulgaris*. The compounds of this invention are also antihypertensive.

The utility of the instant compounds in respect of *B. subtilis*, *S. paratyphi A*, *T. vaginalis*, *T. mentagrophytes*, and *C. vulgaris* can be demonstrated by the standardized tests described in U.S. Pat. No. 3,845,038. In said tests, 1-(2-azidoethyl-2-methyl-5-nitroimidazole, the product of Example 3 hereinafter, was found active at 100, 1000, 1, 1000, and 1000 mcgm per ml, respectively.

The utility of the instant compounds in respect of *S. epidermidis*, *C. perfringens*, and *T. foetus* can be demonstrated by the standardized test described in U.S. Pat. No. 3,882,136. In said tests, 1-(2-azidoethyl)-2-methyl-5-nitroimidazole was found active at 1000, 100, and 0.1 mcgm per ml, respectively.

The utility of the instant compounds in respect of *D. desulfuricans* can be demonstrated by a standardized test whereby fluid thioglycollate medium (manufactured by Baltimore Biological Laboratories or Difco) is prepared as recommended by the manufacturer, sterilized, and inoculated with 1% by volume of a 24-hour culture of *D. desulfuricans*. Meanwhile, compound is dissolved or ultrasonically suspended in sterile distilled water at a concentration of 1000 mcgm per ml. Serial dilutions of the resultant mixture with sterile distilled water afford additional compound preparations containing 100, 10, 1, and 0.1 mcgm of compound per ml. To 0.1 ml of each compound preparation is added 0.9 ml of the inoculated medium. The mixtures thus obtained are anaerobically incubated for 24 hours at 37°C and then examined grossly for turbidity, using a mixture of 0.1 ml of sterile distilled water with 0.9 ml of inoculated medium likewise incubated as control. A compound is considered active if, at the maximum concentration tested, no turbidity is exhibited and no aberrancy is apparent in respect of the control. Four different strains of *D. desulfuricans* identified by Searle code numbers 1620–49, 1620–50, 1620–51, and 1620–52 are commonly used in these tests. 1-(2-Azidoethyl)-2-methyl-5-nitroimidazole was found active at 0.1 mcgm per ml in this test.

The antihypertensive utility of the instant compounds can be demonstrated by the standardized test described in U.S. Pat. No. 3,455,921. 1-(2-Azidoethyl)-2-methyl-5-nitroimidazole was found active at 10 mg per kg in this test.

The activity of 1-(2-azidoethyl)-2-methyl-5-nitroimidazole in the various tests hereinbefore referred to is specified merely for purposes of illustration, and is accordingly not to be construed as either delimiting or exclusionary.

Those skilled in the art will recognize that observations of activity in standardized tests for particular biological effects are fundamental to the development of valuable new drugs, both veterinary and human. Distinct from these applications, compounds active vs. *D. desulfuricans* are adapted to facilitate the production of petroleum and natural gas by counteracting (1) the clogging of oilbearing strata and recovery equipment and (2) the contamination of gas wells with hydrogen sulfide caused by such organisms, whereas antialgal compounds serve to condition boiler feed water and the like.

Preparation of the basic amines of this invention proceeds by warming sodium azide in N,N-dimethylformamide with halides or sulfonates having the formula

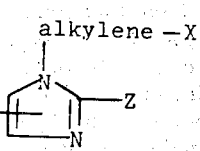

wherein X and Z are defined as before and X' represents chlorine or a radical of the formula

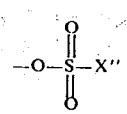

in which X'' represents alkyl or tolyl. The acid addition salts of the invention are prepared by contacting the basic amines with inorganic or strong organic acids wherein the anions are defined by T as set forth above, using an inert solvent medium if desired.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 8 parts of 1-(2-chloroethyl)-2-methylimidazole (U.S. Pat. No. 3,882,136) in 200 parts of N,N-dimethylformamide is added a slurry of 5 parts of sodium azide in 100 parts of N,N-dimethylformamide. The resultant mixture is stirred for 2 hours at approximately 65°, then cooled and thereupon diluted with 600 parts of water. Sufficient potassium carbonate is added to insure basicity. The mixture thus obtained is extracted with chloroform. The chloroform extract is dried over anhydrous magnesium sulfate and stripped of solvent by vacuum distillation, affording 1-(2-azidoethyl)-2-methylimidazole as the residue. The product has the formula

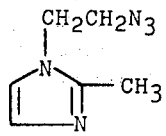

B. To a solution of 4 parts of 1-(2-azidoethyl)-2-methylimidazole in approximately 40 parts of 2-propanol is added 10 parts of a 20% solution of hydrogen chloride in 2-propanol. The precipitate which results (formation of which can be speeded by introducing a small amount of anhydrous ether) is isolated by filtration, washed with anhydrous ether, dried in air, and recrystallized from a mixture of 2-propanol and anhydrous ether to give 1-(2-azidoethyl)-2-methylimidazole hydrochloride melting at 132°–133.5°.

EXAMPLE 2

A. A mixture of 5 parts of 1-(2-chloroethyl)-5-nitroimidazole [Arzneimittel-Forsch, 16, 23 (1966)], 3 parts of sodium azide, and 125 parts of N,N-dimethylformamide is stirred for 3 hours at approximately 75°, then cooled and thereupon diluted with 250 parts of water. Sufficient potassium carbonate is added to insure basicity. The mixture thus obtained is extracted with toluene. The toluene extract is washed with water, dried over anhydrous potassium carbonate, and stripped of solvent by vacuum distillation. The residual oil is 1-(2-azidoethyl)-5-nitroimidazole. The product has the formula

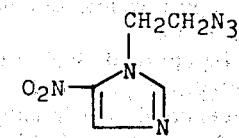

B. To a solution of 6 parts of 1-(2-azidoethyl)-5-nitroimidazole in 20 parts of 2-propanol is added 7 parts of a .20% solution of hydrogen chloride in 2-propanol. The resultant precipitate is recrystallized from a mixture of 2-propanol and methanol to give 1-(2-azidoethyl)-5-nitroimidazole hydrochloride which, washed with 2-propanol and dried in air, sinters at 155° and melts in the range 167°–173° with decomposition.

EXAMPLE 3

To 10 parts of sodium azide is added a solution of 32 parts of 2-(5-nitro-2-methyl-1-imidazolyl)ethyl methanesulfonate (Ger. Pat. No. 2,030,314) in 250 parts of warm N,N-dimethylformamide. The resultant mixture is stirred at approximately 50° for 6 hours, then diluted with 1000 parts of cold water. Sufficient potassium carbonate is added to insure basicity. The mixture thus obtained is extracted with toluene. The toluene extract is washed with water, dried over anhydrous potassium carbonate, and stripped of solvent by vacuum distillation, affording 1-(2-azidoethyl)-2-methyl-5-nitroimidazole as a yellow oil which is further purified by crystallization from ether. Isolated by filtration, washed with a 1:1 mixture of ether and hexane, and dried in air the purified product melts at 53°–54°. It has the formula

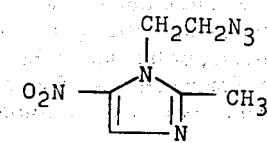

EXAMPLE 4

A. Substitution of 5 parts of 1-(2-chloroethyl)-2-ethyl-5-nitroimidazole [Arzneimittel-Forsch, 16, 23 (1966)], for the 1-(2-chloroethyl)-5-nitroimidazole called for in Example 2A affords, by the procedure there detailed, 1-(2-azidoethyl)-2-ethyl-5-nitroimidazole.

B. To a solution of 1 part of 1-(2-azidoethyl)-2-ethyl-5-nitroimidazole in 10 parts of 2-propanol is added just sufficient 25% hydrogen chloride in 2-propanol to induce acidity, followed by approximately 20 parts of anhydrous ether. The precipitate thrown down is isolated by filtration, washed with anhydrous ether, and dried in air. The product thus isolated is 1-(2-azidoethyl)-2-ethyl-5-nitroimidazole hydrochloride.

EXAMPLE 5

A. Substitution of 5 parts of 1-(3-chloropropyl)-2-methyl-5-nitroimidazole (U.S. 3,882,136) for the 1-(2-chloroethyl)-5-nitroimidazole called for in Example 2A affords, by the procedure there detailed, 1-(3-azidopropyl)-2-methyl-5-nitroimidazole.

B. To a solution of 5 parts of 1-(3-azidopropyl)-2-methyl-5-nitroimidazole in 50 parts of 2-propanol is added 4 parts of a 22% solution of hydrogen chloride in 2-propanol, followed by approximately 150 parts of anhydrous ether. The precipitate which forms is isolated by filtration, washed with anhydrous ether, and dried in vacuo. The product thus obtained is 1-(3-azidopropyl)-2-methyl-5-nitroimidazole hydrochloride, a colorless solid melting in the range 110°–121°.

EXAMPLE 6

Substitution of 6 parts of 1-(3-chlorobutyl)-2-methyl-5-nitroimidazole (U.S. Pat. No. 3,882,136) for the 1-(2-chloroethyl)-5-nitroimidazole called for in Example 2A affords, by the procedure there detailed, 1-(3-azidobutyl)-2-methyl-5-nitroimidazole.

EXAMPLE 7

A mixture of 2 parts of 2-(5-nitro-2-phenyl-1-imidazolyl)ethyl methanesulfonate (U.S. Pat. No. 3,882,136), 2 parts of sodium azide, and 50 parts of N,N-dimethylformamide is stirred at approximately 70° for 3 hours, then cooled and thereupon diluted with 30 parts of water. Sufficient potassium carbonate is added to insure basicity. The mixture thus obtained is extracted with toluene. The toluene extract is washed with water, dried over anhydrous potassium carbonate, and stripped of solvent by vacuum distillation. The residue is 1-(2-azidoethyl)-5-nitro-2-phenylimidazole.

EXAMPLE 8

Substitution of 2 parts of 2-[2-(p-fluorophenyl)-5-nitro-1-imidazolyl]ethyl methanesulfonate (U.S. Pat. No. 3,882,136) for the 2-(5-nitro-2-phenyl-1-imidazolyl)ethyl methanesulfonate called for in Example 7 affords, by the procedure there detailed, 1-(2-azidoethyl)-2-(p-fluorophenyl)-5-nitroimidazole, which is further purified by dissolving it in anhydrous ether, treating the ether solution with decolorizing charcoal, stripping the solvent by vacuum distillation, crystallizing the residue from 2-propanol, washing the crystals with 2-propanol, and drying them in vacuo. The product thus purified melts in the range 58°–65°.

EXAMPLE 9

Substitution of 5 parts of 2-[2-(o-iodophenyl)-5-nitro-1-imidazolyl]ethyl methanesulfonate (U.S. Pat. No. 3,882,136) for the 2-(5-nitro-2-phenyl-1-imidazolyl)ethyl methanesulfonate called for in Example 7 affords, by the procedure there detailed, 1-(2-azidoethyl)-2-(o-iodophenyl)-5-nitroimidazole.

EXAMPLE 10

To 2 parts of sodium azide is added a solution of 5 parts of 2-(2-methyl-4-nitro-1-imidazolyl)ethyl methanesulfonate (U.S. Pat. No. 3,882,136) in 60 parts of N,N-dimethylformamide. The resultant mixture is stirred at approximately 55° for 4 hours, then cooled and thereupon partitioned between water and toluene. The toluene phase is separated, washed with water, dried over anhydrous magnesium sulfate, and stripped of solvent by vacuum distillation. Crystallization of the residual oil from a mixture of ethyl acetate and hexane affords 1-(2-azidoethyl)-2-methyl-4-nitroimidazole as colorless crystals melting at 73°–75°. The product has the formula

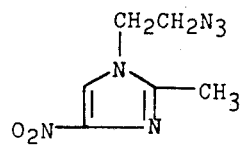

What is claimed is:

1. A compound of the formula

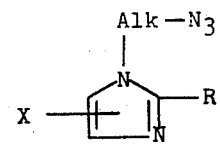

wherein R represents hydrogen, alkyl containing fewer than 8 carbons, phenyl, or halophenyl; Alk represents alkylene containing more than 1 and fewer than 5 carbons; and X represents hydrogen or nitro.

2. A compound according to claim 1 which is 1-(2-azidoethyl)-2-methylimidazole.

3. A compound according to claim 1 which is 1-(2-azidoethyl)-5-nitroimidazole.

4. A compound according to claim 1 having the formula

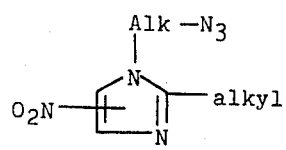

wherein the 2-alkyl substituent called for contains fewer than 8 carbons and Alk represents alkylene containing more than 1 and fewer than 5 carbons.

5. A compound according to claim 1 having the formula

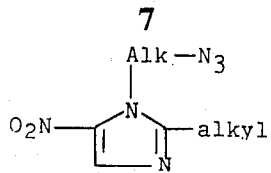

wherein the 2-alkyl substituent called for contains fewer than 8 carbons and Alk represents alkylene containing more than 1 and fewer than 5 carbons.

6. A compound according to claim 1 having the formula

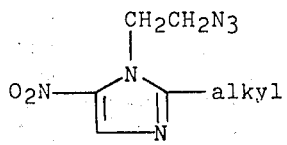

wherein the 2-alkyl substituent called for contains fewer than 8 carbons.

7. A compound according to claim 1 which is 1-(2-azidoethyl)-2-methyl-5-nitroimidazole.

8. A compound according to claim 1 having the formula

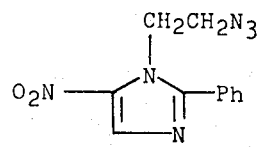

wherein Ph represents phenyl optionally substituted by 1 halogen.

9. A compound according to claim 1 which is 1-(2-azidoethyl)-2-(p-fluorophenyl)-5-nitroimidazole.

10. A compound according to claim 1 which is 1-(2-azidoethyl)-2-methyl-4-nitroimidazole.

* * * * *

UNITED STATES PATENT AND TRADEMARK OFFICE
CERTIFICATE OF CORRECTION

PATENT NO. : 3,962,274
DATED : June 8, 1976
INVENTOR(S) : Ernest F. Levon

It is certified that error appears in the above-identified patent and that said Letters Patent are hereby corrected as shown below:

Column 4, line 37, ".20%" should read -- 20% --.

Signed and Sealed this

Nineteenth Day of October 1976

[SEAL]

Attest:

RUTH C. MASON
Attesting Officer

C. MARSHALL DANN
Commissioner of Patents and Trademarks